United States Patent [19]

Overbeek

[11] 4,292,251

[45] Sep. 29, 1981

[54] 11β-SUBSTITUTED STEROIDS

[75] Inventor: Gerhard A. Overbeek, Nijmegen, Netherlands

[73] Assignee: Akzona Incorporated, Asheville, N.C.

[21] Appl. No.: 873,784

[22] Filed: Jan. 31, 1978

[30] Foreign Application Priority Data

Feb. 10, 1977 [NL] Netherlands .......................... 7701384

[51] Int. Cl.³ ............................ C07J 1/00; C07J 11/00
[52] U.S. Cl. ................................. 260/397.3; 260/239.5; 260/239.55 C; 260/397.45; 260/397.5
[58] Field of Search ................... 260/397.5 A, 397.45, 260/239.5, 239.55 C, 397.3, 397.5; /Steroids MS File

[56] References Cited

U.S. PATENT DOCUMENTS

| | | | |
|---|---|---|---|
| 3,299,108 | 1/1967 | Baran et al. | 260/397.5 |
| 3,377,365 | 4/1968 | Baran | 260/397.5 |
| 3,377,366 | 4/1968 | Baran et al. | 260/397.45 |
| 3,465,010 | 9/1969 | Baran | 260/397.5 |
| 3,755,301 | 8/1973 | Baran et al. | 260/239.55 R |
| 3,922,292 | 11/1975 | Torelli et al. | 260/397.1 |
| 3,927,046 | 12/1975 | Van den Broek | 260/397.3 |
| 3,983,144 | 9/1976 | Leemhuis | 260/397.3 |

FOREIGN PATENT DOCUMENTS

| | | |
|---|---|---|
| 2235949 | 1/1975 | France . |
| 7408041 | 12/1974 | Netherlands . |
| 1255345 | 12/1971 | United Kingdom . |

*Primary Examiner*—Ethel G. Love
*Attorney, Agent, or Firm*—Robert H. Falk; Charles A. Wendel; Francis W. Young

[57] ABSTRACT

Novel and biologically active 11β-substituted steroids of the oestrane series are disclosed having the formula

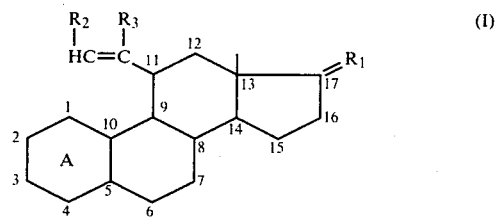

wherein (a) $R_1$ is O or $(\alpha Y)(\beta Z)$, wherein Y is selected from the group consisting of H, unsaturated aliphatic hydrocarbons of two to about four carbon atoms, saturated aliphatic hydrocarbons of about one to four carbon atoms, and Z is a free, esterified, or etherified hydroxy group;

(b) $R_2$ is H and $R_3$ is H or $CH_3$; in the alternative, $R_2$ and $R_3$ together constitute a carbon—carbon bond; and (c) ring A has the structure

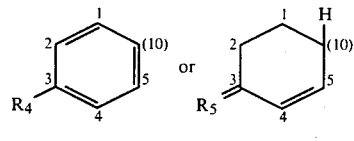

wherein $R_4$ in compound (II) is a free, esterified, or etherified hydroxyl group, and
$R_5$ in compound (III) is O or is two hydrogens.

The new steroids possess oestrogenic, antioestrogenic, progestational, ovulation-inhibiting, uterotropic, androgenic, and anabolic properties for therapeutic administration. Administration may be accomplished via pharmaceutically acceptable compositions containing these compounds in a parenteral, oral or enternal manner (for example, liquid presentations as solutions, suspensions, emulsions, ointments, pastes and solid pharmaceutical presentations such as tablets, pills, capsules and dragees) to take advantage of the recited properties.

29 Claims, No Drawings

11β-SUBSTITUTED STEROIDS

BACKGROUND OF THE INVENTION

1. Field of the Invention

The invention relates to novel steroids of the oestrane series, substituted in the 11β-position, and to pharmaceutical formulations containing these steroids having oestrogenic, anti-oestrogenic, progestational, ovulation-inhibiting, uterotropic, androgenic and anabolic properties. More particularly, the 11β-substituent is an unsaturated group containing two to three carbon atoms.

2. Prior Art and Other Information

Steroids of the oestrane series substituted in the 11β-position are known. For example, 11β-alkyloestranes are described in U.S. Pat. No. 3,325,520, United Kingdom Pat. No. 1,367,735 and U.S. Pat. No. 3,983,144, while 11β-alkoxyoestranes are described in British Pat. No. 1,342,948. Oestranes substituted in the 11β-position by a halomethyl group or an optionally esterified or etherified hydroxymethyl group, are shown in U.S. Pat. No. 3,972,906.

Wechter, U.S. Pat. No. 2,897,198 (1959) discloses certain 11β-alkene-11β-hydroxy-5β-pregnanes useful in the treatment of hypertension, nervous disorders and related illnesses as tranquilizers and sedatives for humans and animals. 11β-alkyl or alkyl-11α-hydroxy (and related) androstanes and pregnanes are also disclosed having anaesthetic properties in Cook et al., U.S. Pat. No. 3,953,429 (1976). John S. Baran in U.S. Pat. Nos. 3,346,602; 3,465,010 and 3,652,606 show 11β-alkyl, rather than 11β-alkenyl substituents, with the compounds '602 useful for their hypocholesterolemic activity, the compounds of '010 for their progestational and deciduogenic activity, the compounds of '606 for their androgenic, anabolic, anti-bacterial, and antifungal activities.

SUMMARY OF THE INVENTION

A new group of steroids of the oestrane series, substituted in the 11β-position possessing interesting and extremely useful biological properties has been found, said steroids being oestrane compounds substituted in the 11β-position by an unsaturated aliphatic hydrocarbon group containing 2 to 3 carbon atoms, and being of the general formula

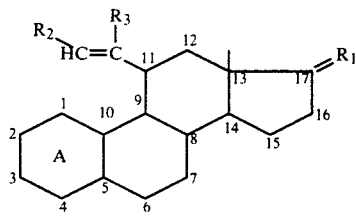

wherein (a) $R_1$ is O or (αY) (βZ), wherein Y is selected from the group consisting of H, unsaturated aliphatic hydrocarbons of two to about four carbon atoms, saturated aliphatic hydrocarbons of about one to four carbon atoms, and Z is a free, esterified or etherified hydroxy group;

(b) $R_2$ is H and $R_3$ is H or $CH_3$; in the alternative, $R_2$ and $R_3$ together constitute a carbon—carbon bond; and (c) ring A has the structure

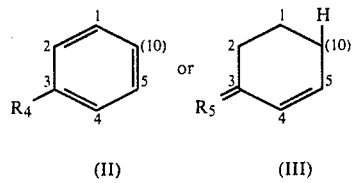

wherein $R_4$ is a free, esterified or etherified hydroxyl group and $R_5$ is O or is two hydrogens.

Preferably, $R_4$ is OH when A is structure (II). Of course, $R_5$ is O or two hydrogens (shorhand "$H_2$") when A is structure III. $R_1$ is O, and in the alternative, (1) Y is preferably H, alkyl of 1 to 2 carbons, ethynyl or allyl and (2) Z is OH, or esterified or etherified hydroxy with an ester or ether group of two to fifteen carbon atoms.

The new compounds prove to possess a surprising range of oestrogenic, anti-oestrogenic, progestational, ovulation-inhibiting, uterotropic, androgenic and anabolic properties.

Remarkable is the considerable and surprising increase in oestrogenic and ovulation-inhibiting activities of the new 11β-substituted 17α-ethynyl nandrolone compounds (in comparison to the corresponding compounds devoid of substituents in the 11β-position), whereas the increase in progestational activity is far less. In other words, the 11β-substitution is associated with a pronounced and remarkable dissociation and a variety of biological activities. The strong anti-oestrogenic properties make the new compounds interesting for their potency for use in the treatment of oestrogen-dependent carcinoma.

The new compounds may be used for therapeutic purposes. The invention therefore also relates to a process for the preparation of pharmaceutical formulations, whereby the new compounds are provided in a form, as known to those skilled in the art, suitable for therapeutic purposes. To this direct end, and generally after admixture with excipients and optionally with other active ingredients, the novel compounds are processed to give dosage forms suitable for parenteral or enteral administration, for example, solutions, suspensions, emulsions, ointments, pastes and solid pharmaceutical presentations, such as tablets, pills, capsules and dragees for oral administration.

DESCRIPTION OF THE PREFERRED EMBODIMENTS

The new compounds may be prepared in various ways. It is, for example, possible to start from an 11,11-methylene- or 11,11-ethylidene-steroid of the oestrane series. These starting materials are described in U.S. Pat. No. 3,927,046, the latter being incorporated herein in full by reference. See in particular column 2, lines 1-2, and column 3, lines 1-42.

With such a steroid, the 11,11-alkylidene group is first converted into an 11β-(1'-hydroxy)-alkyl group, for example with diborane and hydrogen peroxide in an etheric solvent such as tetrahydrofuran, diglyme and diethylether. [See Example I(c)]. The hydroxy group in the 11β-substituent is subsequently oxidised to the oxo group, for example with chromium trioxide or with dicyclohexylcarbodi-imide/dimethyl sulphoxide, so that the 11β-formyl or 11β-acetyl compound respectively is obtained [see Examples I(i), III(a), and V(a)].

The oxo group in the 11β-acetyl compound is converted into the hydrazone by reaction with hydrazine, usually in high-boiling alcohols at reflux temperature (see Example I(j)) after which the hydrazone is reacted with iodine in etheric solvents, such as THF, to give the 11β-(1'-iodo)vinyl compound (Example I(k)); dehydroiodination of this compound by heating with a base in an alcohol, for example with KOH or K-t.butylate in boiling ethanol (Example I(l)), gives the 11β-ethynyl compound. The 11β-vinyl compound can be obtained by treating, for example, the 11β-(1'-iodo)-vinyl compound with Na in an alcohol or with Zn in pyridine and glacial acetic acid (Example XII), or by partially hydrogenating the 11β-substituent in the 11β-ethynyl compound with the aid of a metal catalyst, for example a palladium or platinum catalyst. With the 11β-formyl compound, the number of carbon atoms in the 11β-substituent is increased to 2 by reaction with a suitable Wittig reagent or a suitable Grignard reagent, and the 11β-group thus obtained is further modified as necessary to give the desired 11β-substituent (see Examples III(b) and (c), IV and V(b) and (c)).

A suitable Wittig reagent is a phosphorane of general formula:

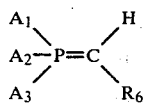

wherein $A_1$, $A_2$ and $A_3$ represent alkyl or aryl groups and $R_6$ is H or halogen. $A_1$, $A_2$ and $A_3$ are preferably phenyl groups so that the preferable phosphoranes are the triphenyl-phosphoryl-alkylidene compounds. See column 4, lines 5–10 of U.S. Pat. No. 3,927,046 for the preparation of these phosphoranes.

Because of the instability of the Wittig reagent, it is preferably prepared in situ. The reaction with the 11β-formyl-steroid is therefore usually performed by adding the steroid or a solution thereof to a mixture of a suitable phosphonium halide and a suitable base in the presence of an appropriate organic solvent and with exclusion of oxygen, for example under a nitrogen atmosphere.

Suitable bases are (1) alkali metal compounds of aliphatic, aromatic or araliphatic hydrocarbons (for example butyl-lithium, phenyl-lithium or triphenylmethylsodium, (2) alkyl-magnesium halides (for example ethyl magnesium bromide), (3) alkali metal amides (for example sodamide), (4) alkali metal alkoxides (for example, sodium ethoxide) and (5) dimsyl-sodium (the reaction product of sodium hydride and dimethyl sulphoxide). Suitable solvents are (1) dimethyl sulphoxide/pyridine, (2) aliphatic ethers (for example dimethyl ether, di-ethyl ether, dioxan or tetrahydrofuran) and (3) aromatic hydrocarbons (for example benzene or toluene).

If the Wittig reagent in which $R_6 = H$ is used, then the 11β-vinyl compound is obtained. If $R_6$ is halogen (for example a chlorine atom), then the product of the Wittig reaction is an 11β-(2'-halo)-vinyl compound, which on dehydrohalogenation, (example-boiling in alkaline ethanol) gives the corresponding 11β-ethynyl compound.

A suitable Grignard reagent is $CH_3M$, where M is an alkali metal, preferably lithium, or Mghal, where hal represents a halogen atom, preferably Cl or I. The reaction of the 11β-formyl compound with the Grignard reagent then gives an 11β-(1'-hydroxy)-ethyl compound, which is converted into a compound with the desired 11β-substituent in the way already indicated above.

The 11β-isopropenyl compound ($R_3 = CH_3$) is obtained by allowing the 11β-acetyl compound to react with the Wittig reagent, specified above, in which $R_6 = H$.

In the preparation of the new compounds, it is also possible to start from an 11-oxo compound of the oestrane series and to expose this to the action of the Wittig reagent

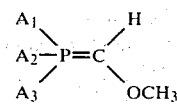

An 11,11-methoxymethylene compound is then obtained, and this is hydrolysed with acid to the 11β-formyl compound. This latter compound may then be converted into a compound with the desired 11β-substituent in the way indicated above (see Example XI).

An 11-oxo compound of the oestrane series can also be reacted with TosMIC (toluene sulphonylmethylisocyanide) in an etheric solvent, such as for example dimethylether or tetrahydrofuran, in the presence of a base, such as for example K-t.butylate (which may be added to the reaction mixture dissolved in a 1:1 mixture of t.-butanol and dimethylether or tetrahydrofuran) to give the corresponding 11β-cyano compound and reacting the cyano compound with $CH_3X$, wherein X is Li or Maghalogen, e.g. MgBr, to give an imine which is readily hydrolysed with acid to the 11β-acetyl compound. (Example XVI). This latter compound may then be converted into a compound with the desired 11β-substituent in the way indicated above.

In the reactions noted above, vulnerable groups present elsewhere in the steroid molecule are temporarily protected in the usual way known to those in the art [see Examples I(a), I(b), I(d), I(f), I(g), II(a), VI(a), VII(a)]. A 17-oxo group present is, for example, protected as a ketal, a 3-oxo-$\Delta^4$-system present, for example, as a ketal, thioketal, enolether or enamine. A hydroxy group in position 3 and/or 17 or in the 11β-substituent is optionally protected in the form of an ether or an ester, such as the methyl ether, the ethoxyethyl ether, the tetrahydropyranyl ether, the benzoate or the acetate. The removal of protecting groups is performed as known in the art, e.g. by hydrolysis in acid or alkaline medium.

If a steroid with an aromatic A ring is used as starting material, and a steroid with a 3-oxo-$\Delta^4$ system is required as end-product, it may be advantageous to interrupt the consecutive series of reactions in order to carry out a Birch reduction of ring A. For example, if 11,11-(E)-ethylidene-oestrone 3-methylether 17-ethylene ketal is used as starting material, then the 11β-substituent is first converted into the 11β-(1'-hydroxy)-ethyl group with diborane and hydrogen peroxide [see Example I(c)]. The hydroxy group in this 11β-substituent is subsequently protected, for example as 1"-ethoxyethyl ether [see Example I(d)], after which ring A is reduced by the method of Birch (reduction with an alkali metal in liquid ammonia), followed by treatment of the $\Delta^{2,5(10)}$-3-enolether obtained with acid [see Example I(e)]. The further reactions necessary to convert the 11β-substituent to the desired end-product are then performed [see Examples I(f)–I(m)].

In this way, the necessity of performing a Birch reduction of an aromatic A ring in the presence of an unsaturated 11β-substituent, through which the yield of the desired end-product could possibly be adversely affected by partial reduction of the 11β-substituent, is avoided.

The substituent in position 13 is already present in the starting material.

The substituents in positions 3 and/or 17, insofar as they are not already present, may still be introduced in a way which is in itself known to those in the art.

A 3-oxo group present may optionally be removed to prepare the 3-desoxo compound [Example VIII].

To this end, the 3-oxo group is converted into the thioketal group by reaction with a mercaptan or di-thiol in the presence of $BF_3$, the etherate thereof or $ZnCl_2$ [Example VII(a)]. The thioketal group is then cleaved reductively (for example, by treatment with an alkali metal, preferably lithium, in the presence of liquid ammonia, or of a lower aliphatic primary amine such as methylamine or ethylamine).

For the preparation of 3-desoxo compounds use is preferably made of a 3-desoxo steroid as starting material, or the reaction sequence for the introduction of the 11β-substituent is interrupted in a suitable place for the cleavage of the 3-oxo or 3-hydroxy group, as indicated above with respect to the Birch reduction of an aromatic A-ring.

The substituents desired in the 17-position may already be present in the starting materials or they may yet be introduced in ways which are in themselves known.

A 17-hydroxy group present may be oxidized to a 17-oxo group, for example, by the Oppenauer method or with chromium trioxide [Example VIII(b)]. A 17-oxo group present may, if desired, be reduced to a 17-hydroxy group, for example, by reduction with $NaBH_4$ in alkaline methanol [Examples V(c), VII(b)].

The introduction of a saturated or unsaturated alkyl group annexed to the 17-position is effected by reacting the 17-oxo steroid with a metal derivative of a saturated or unsaturated aliphatic hydrocarbon, optionally followed by reduction of the side-chain thus introduced. The metal derivative may be a Grignard compound, for example, the magnesium bromide of the hydrocarbon concerned, or an alkyl-lithium compound [Example II(c)].

A special way of performing the condensation reaction for the preparation of the 17β-hydroxy-17α-alkynyl compounds consists of reacting the 17-oxo steroid with a hydrocarbon containing a triple bond, for example acetylene, in the presence of an alkali metal or an alkali metal compound such as an alkali metal amide or alkoxide, or with a metal compound of an acetylenic hydrocarbon such as an alkali metal or alkaline earth metal compound, for example, potassium acetylide [see Example II(b), VI(b)]. Once the alkynyl compound is obtained, hydrogenation in the presence of a Pd catalyst may produce a desired alkenyl result [Example IX].

The hydrocarbon group optionally present in position 17 of the final product may, for example, be a methyl, ethyl, propyl, butyl, isopropyl, vinyl, propenyl, isopropenyl, allyl, methallyl, ethynyl, propynyl, propargyl, butynyl, butadienyl, butadiynyl, propadienyl or butenyl group.

The ester hydroxy group optionally present in position 3 and/or 17 of the final product may be derived from an inorganic acid, such as phosphoric acid, or from a saturated or unsaturated organic carboxylic acid with 1–18 carbon atoms. The conversion of a hydroxy group into an ester group may be effected in a way known in itself, for example by using a derivative thereof, such as the anhydride or halide [see Examples II(c), V(d), VII(e)]. The esterification of the 17β-hydroxy group which has been formed during the 17α-alkylation, may also be effected by allowing the reaction product of the condensation of the 17-oxo steroid with a metal derivative of an unsaturated hydrocarbon, to react, without preceding hydrolysis, with the appropriate acid or a functional derivative thereof. The esterification may, for example, also be achieved by allowing the steroid to react with an anhydride of a suitable carboxlic acid, such as acetic anhydride, in the presence of 4-dimethylaminopyridine, and preferably also in the presence of a tertiary amine such as trimethylamine.

As examples of suitable carboxylic acids which can be used in the esterification, the following are given: formic acid, acetic acid, propionic acid, butyric acid, valeric acid, caproic acid, undecanoic acid, lauric acid, tridecanoic acid, myristic acid, pentadecanoic acid, oleic acid, palmitic acid, stearic acid, adamantane-carboxylic acid, trimethylacetic acid, di-ethylacetic acid, cyclohexane-carboxylic acid, cyclopentylpropionic acid, cyclohexylbutyric acid, cyclohexylpropionic acid, undecenoic acid, benzoic acid, phenylacetic acid, phenylpropionic acid, phenylbutyric acid, fumaric acid, malonic acid, succinic acid, glutaric acid, pimelic and tartaric acid. As noted, functional derivatives of these acids, such as the anhydrides or acid chlorides, may also be used.

The ether hydroxy groups occuring in the end-products in position 3 and/or 17 may be derived from an aliphatic, aromatic, araliphatic or heterocyclic hydrocarbon of less than 18 carbons, for example, methane, ethane, butane, cyclopentane, cyclohexane, benzene, toluene, dihydropyran, vinylethyl ether. Examples of such ether groups are the methyl ether, ethyl ether, butyl ether, cyclopentyl ether, tetrahydropyranyl ether, cyclohexyl ether and ethoxyethyl ether groups.

The esterification is performed by one of the standard methods known to those in the art, i.e. by reacting the steroid alcohol with the acid or the anhydride or halide thereof in the presence of a dehydrating agent or a base.

Although the invention has been described with respect to specific embodiments above, numerous variations and modifications will be come evident to those skilled in the art, without departing from the scope and spirit of the invention as described above and defined in the appended claims, and as shown in the following Examples:

Example I (a) A suspension of 50.6 g 3-hydroxy-11-(E)-ethylidene-$\Delta^{1,3,5(10)}$-oestratrien-17-one in 230 ml methanol was added to a solution of 54 g potassium hydroxide in 580 ml methanol, and 123 ml dimethyl sulphate was then added dropwise with stirring at 20° C. to the solution over a 30-minute period. After stirring for a further 30 minutes, a solution of 75 g potassium hydroxide in 85 ml water was added dropwise at 20° C. over a 30-minute period. The addition of dimethyl sulphate and KOH was repeated once, after which the reaction mixture was stirred for 1 hour at 20° C.

The reaction mixture was subsequently poured into 11.5 ml ice water. The crystals were filtered off, washed with water, and taken up in methylene chloride. The methylene chloride phase was separated from the aqueous phase, dried over sodium sulphate, filtered and evaporated to dryness under vacuum.

Crystallization from methanol gave 48.5 g of the 3-methyl ether of 3-hydroxy-11-(E)-ethylidene-$\Delta^{1,3,5(10)}$-oestratrien-17-one. Melting point: 148°–151° C.;

$[\alpha]_D^{20} = +494°$ (chloroform).

(b) p-toluene-sulphonic acid was added to a solution of 59.4 g 3-methoxy-11-(E)-ethylidene-$\Delta^{1,3,5(10)}$-oestratrien-17-one in 63 ml methylene chloride, 125 ml ethylene glycol, and 19 ml tri-ethyl orthoformate until the mixture showed an obvious acid reaction.

After stirring under reflux for 4 hours, the mixture was cooled to room temperature and pyridine was added. The mixture was then poured into one liter of water. Extraction with methylene chloride resulted in an organic layer which was washed until neutral, dried over sodium sulphate, filtered and evaporated to dryness under vacuum. Crystallization from ethanol containing 1% pyridine gave 57.6 g of the 17-ethylene ketal of 3-methoxy-11-(E)-ethylidene-$\Delta^{1,3,5(10)}$-oestratrien-17-one, melting point 100°–101° C.

(c) 74.3 g sodium borohydride was suspended in 445 ml dry diethylene glycol methyl ether (diglyme) and 320 ml boron trifluoride-etherate was then added dropwise to this suspension over a 6½ hour period. The reaction was performed under nitrogen and the diborane evolved was passed into a stirred solution of 52.5 g 3-methoxy-11-(E)-ethylidene-$\Delta^{1,3,5(10)}$-oestratrien-17-one-17-ethylene ketal in 2180 ml dry tetrahydrofuran at 10° C. Diborane was passed into the mixture for 3 hours at 10° C. and for an additional 3½ hours at room temperature, after which 1050 ml 10% by weight NaOH was cautiously added dropwise to the reaction mixture at 0° C. over a period of about 30 minutes. After stirring for a further 30 minutes at 0° C., a single addition of 258 ml of 30% $H_2O_2$ was performed. The reaction mixture was stirred for a further 3 hours at 0° C. and was then allowed to stand at room temperature for 16 hours. The upper layer was siphoned off, reduced to small bulk under vacuum and, together with the lower layer, poured into ten liters of water. The resultant crystals were filtered off, washed with water, and dissolved, as far as possible, in methylene chloride. The methylene chloride solution was washed with water until neutral, dried over sodium sulphate, and evaporated to dryness under vacuum.

After crystallization from methylene chloride-ether 48.9 g 3-methoxy-11$\beta$-(1'-hydroxy)-ethyl-$\Delta^{1,3,5(10)}$-oestratriene-17-one-17-ethylene ketal were obtained. Melting point: 11.6°–117.5° C.;

$[\alpha]_D^{20} = +52.6°$ (in $CHCl_3$).

(d) 48 mg p-toluene-sulphonic acid was added in portions to a suspension of 43.8 g 3-methoxy-11$\beta$-(1'-hydroxy)-ethyl-$\Delta^{1,3,5(10)}$-oestratrien-17-one-17-ethylene ketal in 500 ml ethyl vinyl ether at 20° C. After stirring for 1 hour at room temperature the reaction was stopped by addition of pyridine, and the reaction mixture was then poured into water. The organic phase was separated from the aqueous phase and the latter was extracted several times with methylene chloride. The combined organic layers were washed with water, dried over sodium sulphate, filtered and evaporated to dryness under vacuum.

52.9 g 3-methoxy-11$\beta$-[1'-(1''-ethoxy)-ethoxy]-ethyl-$\Delta^{1,3,5(10)}$-oestratrien-17-one 17-ethylene ketal (oil) was obtained.

(e) 18 g lithium was added over a period of 5 to 6 hours to a solution of 60.2 g 3-methoxy-11$\beta$-[1'-(1''-ethoxy)-ethoxy]-ethyl-$\Delta^{1,3,5(10)}$-oestratrien-17-one 17-ethylene ketal in 1500 ml liquid ammonia, 600 ml dry tetrahydrofuran and 600 ml dry tert. butanol at $-60°$ C. The reaction mixture was stirred for a further 8 hours at $-60°$ C., after which the ammonia was removed by evaporation and the residue was poured into 1.5 l water. The organic layer was separated from the aqueous layer and the latter was extracted with methylene chloride. The combined organic layers were washed with a saturated solution of sodium chloride, dried over sodium sulphate, filtered, and evaporated to dryness under vacuum. The resultant residue was dissolved in 590 ml acetone with 5.9 ml concentrated hydrochloric acid, and stirred for 1½ hours at room temperature. The reaction mixture was evaporated under vacuum to small bulk, diluted with water and extracted with methylene chloride. The extract was washed with water, dried over sodium sulphate, filtered, and evaporated to dryness under vacuum.

After chromatography over silica gel, 29.5 g 11$\beta$-(1'-hydroxy)-ethyl-$\Delta^4$-oestren-3,17-dione was obtained (M.pt.: 162°–163° C.).

(f) 70 ml acetic anhydride was added to a solution of 27.8 g 11$\beta$-(1'-hydroxy)-ethyl-$\Delta^4$-oestren-3,17-dione in 560 ml dry pyridine. After stirring for 22 hours at room temperature, sufficient ice was added, and the mixture was stirred for a further 30 minutes, after which it was reduced to small bulk under vacuum and poured into 1.5 l ice water. After extraction with methylene chloride, the extract was washed with dilute sulphuric acid followed by water, dried over sodium sulphate, filtered and evaporated to dryness under vacuum.

Crystallization from alcohol gave 26.3 g 11$\beta$-(1'-acetoxy)-ethyl-$\Delta^4$-oestren-3,17-dione, melting point: 175°–176° C.

(g) About 2.65 mg p-toluene-sulphonic acid was added to a solution of 25.1 g 11$\beta$-(1'-acetoxy)-ethyl-$\Delta^4$-oestren-3,17-dione in 330 ml methylene chloride, 195 ml ethylene glycol and and 83.5 ml tri-ethyl orthoformate. After boiling under reflux for 6 hours, the reaction mixture was cooled to room temperature and pyridine was added. Water then added and, after separation of the organic layer, the aqueous layer was extracted with methylene chloride. The extract was added to the organic layer and the whole was washed with water, dried over sodium sulphate, filtered, and evaporated to dryness under vacuum.

Crystallization from alcohol gave 30.5 g 11$\beta$-(1'-acetoxy)-ethyl-$\Delta^5$-oestren-3,17-dione 3,17-di-ethylene ketal, melting point 157°–160° C.

(h) A solution of 5.9 g potassium hydroxide in 65 ml water was added to a solution of 30.5 g 11$\beta$-(1'-acetoxy)-ethyl-$\Delta^5$-oestren-3,17-dione-3,17-diethylene glycol in 650 ml methanol. After boiling under reflux for 5 hours, the mixture was cooled to room temperature and poured into 4 l water. The crystals were filtered off, washed with water and taken up in methylene chloride. The solution thus obtained was dried over sodium sulphate, filtered, and evaporated to dryness under vacuum.

After crystallization from methanol, 18.8 g 11$\beta$-(1'-hydroxy)-ethyl-$\Delta^5$-oestren-3,17-dione-3,17-diethylene-ketal were obtained. Melting point: 234°–243° C.

(i) 15.4 g powdered chromium trioxide was added to a mixture of 25 ml pyridine and 310 ml methylene chloride. The whole was stirred for 15 to 30 minutes at room temperature, after which 15.4 g 11β-(1'-hydroxy)-ethyl-Δ⁵-oestren-3,17-dione-3,17-diethylene ketal was added. After stirring for 16 hours under a nitrogen atmosphere, the reaction mixture was filtered over Hyflo (Johns Manville Corp.) and the filter was washed thoroughly with methylene chloride. The filtrate was washed with a 10% sodium bisulphite solution and with water, dried over sodium sulphate, filtered and evaporated to dryness under vacuum.

Crystallization from ethanol gave 14.3 g 11β-acetyl-Δ⁵-oestren-3,17-dione-3,17-di-ethylene ketal, melting point 179°–180.5° C.

(j) 4 g hydrazine dihydrochloride was added to a suspension of 4.2 g 11β-acetyl-Δ⁵-oestren-3,17-dione-3,17-di-ethylene ketal in 60 ml tri-ethylene glycol, 10 ml hdyrazine hydrate and 5 ml ethanol, and the whole was refluxed in a nitrogen atmosphere for 6 hours. After cooling, the reaction mixture was poured into 600 ml water. The crystals were filtered off, washed with water and dried under vacuum at room temperature. Melting point: 208°–210° C. (decomposition).

(k) A solution of 6.96 g iodine in 21 ml dry tetrahydrofuran was added over a period of about 75 minutes at room temperature and under a nitrogen atmosphere to a solution of 3.08 g 11β-acetyl-Δ⁵-oestren-3,17-dione hydrazone in 210 ml dry THF and 100 ml tri-ethylamine. The reaction mixture was decanted, and the precipitate was washed twice with dry tetrahydrofuran. The filtrate was evaporated to small bulk under vacuum and was then, together with the precipitate, poured into water. After extraction with methylene chloride, washing of the extract with 5% sodium thiosulphate solution and water, and evaporating to dryness, 3.8 g crude 11β-(1'-iodovinyl)-Δ⁵-oestren-3,17-dione-3,17diethylene ketal was obtained and used without further purification.

(l) A mixture of 3.8 g 11β-(1'-ido-vinyl)-Δ⁵-oestren-3,17-dione-3,17-di-ethylene ketal, 7.9 g potassium hydroxide and 95 ml ethanol was refluxed for 90 minutes. After cooling, the reaction mixture was poured into 1 liter ice-water and extracted with methylene chloride. The extract was washed with water, dried over sodium sulphate, filtered and evaporated to dryness under vacuum. The residue was chromatographed over neutral silica gel, using toluene/ethyl acetate (7:3) as eluent, giving 1.5 g 11β-ethynyl-Δ⁵-oestrene-3,17-dione-3,17-di-ethylene ketal.

After crystallization from ethanol, 1.4 g of product were obtained, melting point 183°–186° C. and
$[\alpha]_D^{20} = 0°$ (in CHCl₃)

(m) A mixture of 1.5 g 11β-ethynyl-Δ⁵-oestren-3,17-dione-3,17-di-ethylene ketal, 15 ml acetone and 0.15 ml concentrated hydrochloric acid was stirred for 1½ hours at room temperature. After dilution with water, the reaction mixture was extracted with methylene chloride. The methylene chloride extract was washed with sodium bicarbonate solution, water, dried over sodium sulphate, filtered and evaporated to dryness under vacuum. The residue was chromatographed over silica gel, with toluene/ethyl acetate (7:3) as eluent.

After crystallization from di-ethyl ether/hexane, 0.9 g 11β-ethynyl-Δ⁴-oestrene-3,17-dione was obtained. Melting point: 133°–137° C. and
$[\alpha]_D^{20} = +215.3°$ (in CHCl₃).

EXAMPLE II (a) A mixture of 1.7 g 11β-ethynyl-Δ⁴-oestren-3,17-dione, 5.7 ml ethanol and 1.7 ml tri-ethyl orthoformate was cooled to 0° C. After addition of 7 mg p-toluene sulphonic acid, the mixture was stirred for 3 hours at 0° C. Pyridine was then added, followed by 60 ml water, and the mixture was stirred for a further 60 minutes at 0° C. The crystals were filtered off, washed with 50% by weight ethanol and ½% pyridine, and dried under vacuum at room temperature.

About 1.5 g crude 3-ethoxy-11β-ethynyl-Δ³,⁵-oestradien-17-one was obtained in this way and was used without further purification.

(b) Acetylene was passed through a suspension of 1.82 g potassium t-butoxide in 16 ml dry tetrahydrofuran at 0° C. for 2 hours. This reaction mixture was then cooled to −10° C., and a solution of 1.3 g 3-ethoxy-11β-ethynyl-Δ³,⁵-oestradien-17-one in 28 ml dry tetrahydrofuran was added dropwise over a period of 30 minutes. The mixture was held at −10° C. and stirred while acetylene was passed through for 2 hours. While acetylene was still being passed into the mixture, it was cooled to −30°–40° C. and a solution of 3 ml acetic acid in 3 ml dry tetrahydrofuran was added dropwise. The reaction mixture was then poured into water and extracted with methylene chloride. After working up, the extract was dissolved in 18 ml acetone and 0.18 ml concentrated hydrochloric acid. After stirring at room temperature for 1 hour, the reaction was halted by addition of pyridine and pouring of the reaction mixture into water. With subsequent extraction with methylene chloride and evaporation of the extract, the residue (1.4g) was chromatographed over silica gel and eluted with toluene/ethyl acetate (6:4).

Crystallization from ethanol-water gave 0.6 g 11β,17α-di-ethynyl-17β-hydroxy-Δ⁴-oestren-3-one, melting point 169°–171° C. and
$[\alpha]_D^{20} = +74.5°$ (in CHCl₃).

(c) 1 g 3-ethoxy-11β-ethynyl-Δ³,⁵-oestradien-17-one in 25 ml dry tetrahydrofuran was allowed to react with ethyl lithium. The usual working up gave 0.6 g 11β-ethynyl-17α-ethyl-17β-hydroxy-Δ⁴-oestren-3-one. The 17β-acetate of this compound was prepared. By using allyl magnesium bromide instead of ethyl lithium, 11β-ethynyl-17α-allyl-17β-hydroxy-Δ⁴-oestren-3-one was obtained. The 17β-phenylproprionates were prepared from the 17β-hydroxy compounds noted above.

EXAMPLE III (a) 1.7 g p-toluene sulphonic acid was added to a solution of 156.5 g 11β-hydroxymethyl-Δ⁴-oestren-3,17-dione in 1560 ml methylene chloride, 1100 ml ethanediol and 235 ml tri-ethyl orthoformate. After boiling under reflux for 3 hours, the reaction mixture was cooled and poured into dilute NaHCO₃ solution. After working up by extraction with methylene chloride, the residue was dissolved in 2000 ml methanol. After addition of a solution of 21 g potassium hydroxide in 210 ml water, the reaction mixture was stirred for 1½ hours at room temperaure. It was subsequently poured into 3 l water and extracted with methylene chloride. The extract was washed with water, dried over sodium sulphate, filtered and evaporated to dryness under vacuum to make a crude (11β-hydroxymethyl-Δ⁵⁽¹⁰⁾-oestren-3,17-dione-3,17-diethylene ketal.

(b) 6.2 g of the crude 11β-hydroxymethyl-Δ⁵⁽¹⁰⁾-oestren-3,17-dione-3,17-di-ethylene ketal thus obtained was dissolved in 185 ml acetone and, after cooling to −10° C. to −15° C. 4.9 ml 8 N CrO₃ solution was added dropwise over a period of about 15 minutes. After a reaction time of 5 minutes at −10° C. to −15° C., the excess CrO₃ was removed with a solution of sodium bisulphite. Acetone was removed by distillation under vacuum and the reaction mixture was diluted with water, after which it was extracted with methylene chloride. The extract was washed with water, dried over sodium sulphate, filtered and, after addition of a little pyridine, evaporated to dryness under vacuum. Purification by chromatography on silica gel and crystallization from diethyl ether gave 2 g 11$\beta$-formyl-$\Delta^{5(10)}$-oestren-3,17-dione-3,17-di-ethylene ketal, melting point 117° C. (with decomposition) and $[\alpha]_D^{20} = +73.1°$ (in CHCl₃).

(c) During a period of about 20 minutes, 5.9 ml of a 2.1 M solution of butyl-lithium in hexane was added dropwise at room temperature and under nitrogen to a suspension of 4.3 g chloromethyl-triphenyl phosphonium chloride in 125 ml dry di-ethyl ether. After stirring for a further 15 minutes at room temperature, 0.95 g 11$\beta$-formyl-$\Delta^{5(10)}$-oestren-3,17-dione-3,17-di-ethylene di-ethylene ketal was added, and the reaction mixture was subsequently thoroughly stirred for 1 hour. It was then poured into 500 ml ice water and extracted with methylene chloride.

After working up by chromatography on silica gel, 0.6 g 11$\beta$-(2'-chlorovinyl)-$\Delta^{5(10)}$-oestren-3,17-dione-3,17-di-ethylene ketal (cis/trans ratio 1:3) was obtained.

(d) 0.27 g lithium was cautiously added at about −45° C. and with stirring to a mixture of 20 ml liquid ammonia and 30 mg ferric nitrate (9H₂O). After stirring for a further 15 minutes at −45° C., a solution of 0.55 g 11$\beta$-(2'-chlorovinyl)-$\Delta^{5(10)}$-oestren-3,17-dione-3,17-di-ethylene ketal in 6 ml dry tetrahydrofuran was added dropwise to the grey suspension over a period of about 2 minutes.

After stirring for 45 minutes at −45° C., the ammonia was removed by evaporation and 20 ml water was cautiously added to the residue. The aqueous layer was extracted with methylene chloride. The methylene chloride extract was washed with water, dried over sodium sulphate, filtered and evaporated to dryness under vacuum.

Crystallization from di-ethyl ether gave 0.33 g 11$\beta$-ethynyl-$\Delta^{5(10)}$-oestren-3,17-dione-3,17-di-ethylene ketal, melting point 146°–148° C.

After hydrolysis of the ketal groups with hydrochloric acid in acetone, 0.2 g 11$\beta$-ethynyl-$\Delta^4$-oestren-3,17-dione was obtained, melting point 133°–137° C. and $[\alpha]_D^{20} = +215.3$ (in CHCl₃).

EXAMPLE IV

A suspension of 7.4 g NaH (55% suspension in oil) in 137 ml dry dimethyl sulphoxide was warmed under a nitrogen atmosphere to 70° and stirred at this temperature for 45 minutes. After cooling to room temperature, a solution of 66 g triphenylmethyl phophonium bromide in 285 ml dry di-methyl sulphoxide was added over a 15-minute period, followed by a solution of 11.5 g 11$\beta$-formyl-$\Delta^{5(10)}$-oestren-3,17-dione-3,17-di-ethylene ketal (Example III(a)) in 115 ml dry benzene, again added in 15 minutes. After allowing to react at 70° for 2½ hours under N₂, the reaction mixture was poured into 2.6 liters ice-water. The benzene layer was then separated and washed with water until it became neutral.

The extract was evaporated to dryness and the triphenylphosphine oxide formed was separated with the aid of a hexane/70% methanol partition.

The hexane extract was evaporated to dryness and taken up in 285 ml acetone, whereupon it was stirred for 90 minutes with 1.4 ml concentrated hydrochloric acid. The reaction mixture was subsequently reduced by evaporation to a bulk of 50 ml and poured into water. The crystals were filtered off.

After crystallization from methylene chloride/diethyl ether, 7.1 g 11$\beta$-vinyl-$\Delta^4$-oestren-3,17-dione were obtained, melting point 179°–181° C. and $[\alpha]_D^{20} = +183°$ (in CHCl₃).

EXAMPLE V (a) A solution of 37.9 g 3-methoxy-11$\beta$-hydroxymethyl-$\Delta^{1,3,5(10)}$-oestratrien-17-one-17-ethylene ketal in 260 ml methylene chloride was added to a suspension of 63.4 g chromium trioxide in 100 ml pyridine and 1600 ml methylene chloride.

After stirring for 2½ hours at room temperature, the reaction mixture was filtered through Hyflo. The methylene chloride layer was separated off and washed consecutively with 5% by weight NaHSO₃-aqueous solution, water 2N sulphuric acid and finally with water until neutral. The extract was evaporated to dryness under vacuum and crystallized from methanol.

28.6 g 3-methoxy-11$\beta$-formyl-$\Delta^{1,3,5(10)}$-oestratrien-17-one-17-ethylene ketal of melting point 120.5°–122.5° C. was obtained in this way.

(b) 146 ml of a 20% solution of butyl-lithium in hexane was added dropwise to 172 g triphenyl-methyl phosphonium bromide in 1720 ml dry pyridine. The reaction mixture was boiled under N₂ until all constituents had dissolved, whereupon it was cooled to room temperature and a solution of 28.6 g 3-methoxy-11$\beta$-formyl-$\Delta^{1,3,5(10)}$-oestratrien-17-one-17-ethylene ketal in 86 ml dry toluene was added. After allowing to react at its boiling point for 90 minutes, the reaction mixture was poured into water and extracted with methylene chloride.

The extract was washed consecutively with 6 N sulphuric acid until acid, and with water until neutral, after which it was evaporated to dryness. The residue was taken up in toluene and filtered through 1:10 silica gel. After evaporation to dryness, the pure fractions were crystallized from methylene chloridemethanol.

23 g 3-methoxy-11$\beta$-vinyl-$\Delta^{1,3,5(10)}$-oestratrien-17-one-17-ethylene ketal, of melting point 76.5°–77.5° C. and $[\alpha]_D^{20} = +36.3°$ (in CHCl₃)

were obtained in this way.

(c) A mixture of 1 g 3-methoxy-11$\beta$-vinyl-$\Delta^{1,3,5(10)}$-oestratrien-17-one-17-ethylene ketal and 1.5 g potassium hydroxide in 15 ml tri-ethylene glycol was heated at 200°–210° C. under N₂ for 5 hours. After cooling, the reaction mixture was worked up by extraction with methylene chloride. The residue obtained, in 20 ml acetone, was treated with 0.1 ml concentrated hydrochloric acid at room temperature for 3 hours. After dilution with water and extraction with methylene chloride, 0.6 g crude 3-hydroxy-11$\beta$-vinyl-$\Delta^{1,3,5(10)}$-oestratrien-17-one was obtained. This was dissolved in 10 ml methanol and treated with 0.2 g NaBH₄, dissolved in 1 ml water in which 20 mg sodium hydroxide had already been dissolved. The reaction mixture was stirred for 2 hours at room temperature, after which excess sodium borohydride was removed by cautious addition of 50% acetic acid. After dilution with water, the precipitate was filtered off, washed with water and purified by crystallization.

0.45 g pure 11β-vinyl-Δ$^{1,3,5(10)}$-oestratrien-3,17-diol was obtained in this way, m.pt. 197.5°–199.5° C.; [α]$_D^{20}$ = +95° (in CHCl$_3$:CH$_3$OH 1:1).

(d) By esterification in the usual way, 11β-vinyl-Δ$^{1,3,5(10)}$-oestratrien-3,17β-diol was converted into the 17β-decanoate, the 17β-cyclo-octylacetate and the 17β-valerate via the 3,17β-diester and partial hydrolysis. The 17β-tetrahydropyranyl ether was prepared by etherification.

EXAMPLE VI (a) 4 g 11β-vinyl-Δ$^4$-oestren-3,17-dione and 1.6 ml pyrrolidine in 16 ml methanol were boiled under N$_2$ for 3 hours.

After cooling and separation of the crystals by filtration, 4.1 g 3-pyrrolidino-11β-vinyl-Δ$^{3,5}$-oestradien-17-one was obtained.

(b) 4.1 g 3-pyrrolidino-11β-vinyl-Δ$^{3,5}$-oestradien-17-one was added to a solution of potassium acetylide (prepared from 6.2 g potassium t.butoxide and acetylene) in tetrahydrofurn at 0°–5° C., after which acetylene was continuously passed through the stirred reaction mixture at this temperature for 3 hours.

The reaction mixture was subsequently acidified with 2 N suphuric acid, diluted with water and worked up by extraction with methylene chloride.

The residue obtained by evaporation under vacuum was hydrolysed in a mixture of 78 ml methanol, 12 ml acetic acid, 14 ml water and 11.5 g sodium acetate at the boiling point for 2½ hours.

After working up by means of extraction with methylene chloride, the residue obtained was chromatographed on 1:40 silica gel using the solvent system toluene:ethyl acetate 7:3.

After crystallization from di-ethyl ether, 1.1 g 11β-vinyl-17α-ethynyl-17β-hydroxy-Δ$^4$-oestren-3-one of melting point 182.5°–183.5° C. and
[α]$_D^{20}$ = +31° (CHCl$_3$) was obtained.

(c) Starting from the crude 3-hydroxy-11β-vinyl-Δ$^{1,3,5(10)}$-oestratrien-17-one obtained in Example V(c), 11β-vinyl-17α-ethynyl-Δ$^{1,3,5(10)}$-oestratrien-3,17β-diol was prepared in a way analogous to that described in Example VI(b).

EXAMPLE VII (a) 4.6 ml ethane-dithiol and 4.6 ml BF$_3$-etherate were added at 0° C. and under N$_2$ to a suspension of 4.0 g 11β-vinyl-Δ$^4$-oestren-3,17-dione in 50 ml methanol. After stirring for 1 hour, the precipitate was filtered off, washed with cold methanol and dried under vacuum at 50° C. The 4.8 g of 11β-vinyl-Δ$^4$-oestren-3,17-dione-3-ethylene-dithioketal obtained in this way were used without further purification in the reduction step.

(b) A suspension of 4.8 g 11β-vinyl-Δ$^4$-oestren-3,17-dione-3-ethylene dithioketal in 240 ml methanol was stirred at 0°–5° C. with 2.4 g sodium borohydride for 2 hours.

After excess sodium borohydride had been decomposed with acetic acid, the reaction mixture was poured out and the precipitate was filtered off and dried. The 4.8 g of 11β-vinyl-17α-hydroxy-Δ$^4$-oestren-3-one-3-ethylene dithioketal thus obtained were used without purification in the following step.

(c) 4.6 ml water, followed by 8 ml methyl iodide, were added to a suspension of 4.8 g 11β-vinyl-17β-hydroxy-Δ$^4$-oestren-3-one-3-ethylene dithioketal in 80 ml ethanol (96% by weight). The reaction mixture was boiled for 18 hours, reduced to a volume of about 25 ml by evaporation under vacuum, diluted further with 200 ml water, and extracted with methylene chloride. The residue obtained after removal of solvent under vacuum was chromatographed on 1:100 silica gel using toluene:ethyl acetate (7:3) as solvent system.

Crystallization of the pure fractions from cyclohexane gave 2.8 g 11β-vinyl-17β-hydroxy-Δ$^4$-oestren-3-one, melting point 133° C. and
[α]$_D^{20}$ = +127° (CH$_2$Cl$_2$).

(d) 11β-ethynyl-Δ$^4$-oestren-3,17-dione was converted into 11β-ethynyl-17β-hydroxy-Δ$^4$-oestren-3-one (amorphous; [α]$_D^{20}$ = +6° in CH$_2$Cl$_2$) in a way analogous to that described in Example VII(a)–(c).

(e) The 17β-hydroxy compounds obtained in Examples VII(c) and VII(d) were acylated in the usual way with the appropriate carboxylic acid in pentane/pyridine to give the 17β-decanoate and the 17β-cyclo-octylacetate (oil with [α]$_D^{20}$ = +83.4° in CH$_2$Cl$_2$).

EXAMPLE VIII (a) A solution of 4 g 11β-vinyl-17β-hydroxy-Δ$^4$-oestren-3-one-3-ethylene dithioketal in 20 ml dry tetrahydrofuran was added under a nitrogen atmosphere to a solution of 2.3 g sodium in 90 ml liquid ammonia at −40° C. After stirring for 30 minutes at −40° C., excess sodium was destroyed by the addition of 15 ml ethanol, and the ammonia was removed by evaporation. The residue was diluted with water. The precipitate formed was filtered off, dried under vacuum and purified by means of column chromatography. 2.1 g pure 11β-vinyl-Δ$^4$-oestren-17β-ol was obtained in this way.

(b) Chromic acid oxidation of 11β-vinyl-Δ$^4$-oestren-17β-ol gave 11β-vinyl-Δ$^4$-oestren-17-one, which was converted into 11β-vinyl-17α-ethynyl-Δ$^4$-oestren-17β-ol in the way described in Example VI(b).

EXAMPLE IX

A suspension of 0.1 g 5% Pd on CaCO$_3$ in 20 ml benzene was saturated with hydrogen, after which a solution of 1 g 11β-vinyl-17α-ethynyl-Δ$^4$-oestren-17β-ol in 20 ml benzene was added. The reaction mixture was hydrogenated at normal pressure and room temperature until 1 equivalent of hydrogen had been taken up. The catalyst was filtered off and the filtrate was evaporated to dryness. The residue was purified by column chromatography on silica gel.

0.5 g pure 11β, 17α-divinyl-Δ$^4$-oestren-17β-ol was obtained in this way.

EXAMPLE X (a) 1 g 11β-ethynyl-Δ$^{5(10)}$-oestren-3,17-dione-3,17-diethylene ketal was hydrogenated in the way described in Example IX until 1 equivalent of hydrogen had been taken up.

(b) 0.4 g 11β-vinyl-Δ$^{5(10)}$-oestren-3,17-dione-3,17-diethylene ketal was obtained, and this was converted by hydrolysis with hydrochloric acid in acetone into 0.3 g 11β-vinyl-Δ$^4$-oestren-3,17-dione, melting point 179°–181° C.,
[α]$_D^{20}$ = +183° (CHCl$_3$).

EXAMPLE XI 2.6 g sodium hydride (a 55%–60% suspension in oil) was suspended in 50 ml dry DMSO. The reaction mixture was placed in a waterbath at 75° C. for 1 hour and then cooled to room temperature, after which a solution of 21.4 g methoxymethyl-triphenylphoshonium chloride in 70 ml dry dimethyl sulphoxide was added. After stirring for a further 15 minutes at room temperature, a solution of 4.7 g $\Delta^5$-oestren-3,11,17-trione-3,17-di-ethylene ketal in 30 ml dry dimethyl sulphoxide was added. The whole was stirred for 5 hours in a waterbath at 60° C. after which it was poured into 1.5 l ice water. After extraction with methylene chloride and chromatography on silica gel, 2.6 g 11-methoxy-methylene-$\Delta^5$-oestren-3,17-dione-3,17-di-ethylene ketal of melting point 199.5°–202° C. and $[\alpha]_D^{20} = +29.1°$ (1% $CHCl_3$)

was obtained.

The 11-methoxymethylene compound was converted by partial hydrolysis into 11$\beta$-formyl-$\Delta^5$-oestren-3,17-dione-3,17-di-ethylene ketal, from which 11$\beta$-vinyl-$\Delta^4$-oestrene-3,17-dione of melting point 179°–181° C. and $[\alpha]_D^{20} = +183°$ ($CHCl_3$)

was obtained in the way described in Example IV(c).

EXAMPLE XII 7 g sodium was added in portions to a solution of 1.2 g 11$\beta$-iodovinyl-$\Delta^5$-oestren-3,17-dione-3,17-di-ethylene ketal in 55 ml alcohol. The reaction mixture was then refluxed for 3 hours, after which it was reduced to small bulk by evaporation of the alcohol under vacuum.

After dilution with water, the reaction mixture was extracted with methylene chloride. The methylene chloride extract was washed with water, dried over $Na_2SO_4$, filtered and evaporated to dryness under vacuum (0.7 g). With the aid of HCl, 0.4 g 11$\beta$-vinyl-$\Delta^4$-oestren-3,17-dione was obtained in the known way from the residue. Melting point 179°–181° C. and $[\alpha]_D^{20} = +183°$ ($CHCl_3$)

was obtained in the way described in Example IV(c).

EXAMPLE XIII

A suspension of 3.7 g NaH (55% suspension in oil) in 70 ml dry dimethylsulphoxide was heated in a nitrogen atmosphere till 70° C. and then stirred for 45 minutes. After cooling to room temperature a solution of 33 g triphenylmethylphosphoniumbromide in 140 ml dry dimethylsulphoxide and a solution of 6.0 g 11$\beta$-acetyl-$\Delta^5$-oestrene-3,17-dione 3,17-diethylene ketal in 60 ml dry dimethylsulphoxide were added in succession. After stirring the reaction mixture for 3 hours at 70° C. under nitrogen the mixture was poured into 1.3 l ice-water and stirred for $\frac{1}{2}$ hour. The precipitate was filtered off and washed with a cold (0° C.) mixture of methanol and water (1:1) to remove triphenylphosphine-oxide. The residue was dried at 70° C. giving 5.9 g 11$\beta$-isopropenyl-$\Delta^5$-oestrene-3,17-dione 3,17-diethylene ketal, which on hydrolysis in 60 ml acetone and 0.6 ml concentrated hydrochloric acid (stirring for 3 hours at room temperature), extraction with methylene chloride, neutralization of the extract followed by drying over $Na_2SO_4$, filtration and evaporation of the extract until dry, chromatography of the residue on silicagel and crystallization from diethyl ether gave 4.1 g 11$\beta$-isopropenyl-$\Delta^4$-oestrene-3,17-dione.

In a similar way as described in Example VI(a) and (b) 4.1 g 11$\beta$-isopropenyl-$\Delta^4$-oestrene-3,17-dione was converted into 1.2 g 11$\beta$-isopropenyl-17$\alpha$-ethylene-17$\beta$-hydroxy-$\Delta^4$-oestren-3-one.

EXAMPLE XIV

According to the procedure of Example I, however while deleting the steps (d) to and inclussive (h) and using in step (a) ethylvinylether for etherifying the 3-hydroxy group (temporary protection), 25 g 3-hydroxy-11-(E)-ethylidene-$\Delta^{1,3,5(10)}$-oestratriene-17-one was converted into 4.2 g 11$\beta$-ethynyl-3-hydroxy-$\Delta^{1,3,5(10)}$-oestratrien-17-one. Reduction of the 17-ketone according to the procedure of Example VII(b) gave 11$\beta$-ethynyl-$\Delta^{1,3,5(10)}$-oestratriene-3,17$\beta$-diol, whereas ethynylation according to the procedure of Example VI(b) gave 11$\beta$, 17$\alpha$-diethynyl-$\Delta^{1,3,5(10)}$-oestratriene-3,17$\beta$-diol.

EXAMPLE XV (a) According to the procedure of Examples VII(a), VII(b) and VIII(a), 11$\beta$-ethynyl-$\Delta^4$-oestrene-3,17-dione was converted into 11$\beta$-ethynyl-$\Delta^4$-oestren-17$\beta$-ol, from which according to the procedure of Example VIII(b) 11$\beta$,17$\alpha$-diethynyl-$\Delta^4$-oestren-17$\beta$-ol was obtained.

(b) By using in the procedure as described under (a) above allylmagnesiumbromide instead of potassium acetylide 11$\beta$-ethynyl-17$\alpha$-allyl-$\Delta^4$-oestren-17$\beta$-ol was obtained.

(c) In a similar way as described under (a) above 11$\beta$-isopropenyl-$\Delta^4$-oestrene 3,17-dione was converted into 11$\beta$-isopropenyl-17$\alpha$-ethynyl-$\Delta^4$-oestren-17$\beta$-ol.

EXAMPLE XVI (a) In a nitrogen atmosphere, 7.5 g potassium t.-butylate and 65 ml dry t.-butanol were added to a stirred solution of 2.5 g $\Delta^5$-oestrene-3,11,17-trione 3,17-diethylene ketal in 80 ml dry tetrahydrofuran. To this mixture a solution of 2.62 g tosylmethylisocyanide in 20 ml dry tetrahydrofuran was added at room temperature and in the course of 3$\frac{1}{2}$ hours.

After another hour stirring at room temperature the reaction mixture was poured into 1.5 l ice-water and extracted with methylene chloride. The extract was washed with water until neutral, dried over $Na_2SO_4$, filtrated and evaporated in vacuum until dry. Chromatography of the residue over neutral silicagel (elution with hexane/ethylacetate 1:1) and crystallization from ehter/penetane have 0.9 g 11$\beta$-cyano-$\Delta^5$-oestrene-3,17-dione 3,17-diethylene ketal, m.p. 117.5°–118.5° C.

(b) A solution of 0.9 g 11$\beta$-cyano-$\Delta^5$-oestrene-3,17-dione 3,17-diethylene ketal in 20 ml dry tetrahydrofuran was added to a solution of methylmagnesiumbromide in 50 ml dry diethylether (prepared from 2 g magnesium and methylbromide) in a nitrogen atmosphere and at room temperature.

After reflux for 6 hours the reaction mixture was cooled to room temperature and 75 ml 50% acetic acid was added. The mixture was then refluxed for 15 minutes. After cooling and dilution with water the etheric layer was separated from the aqueous layer and the aqueous layer was extracted with diethylether. The ether extract was washed with water until neutral, dried over $Na_2SO_4$, filtrated and evaporated in vacuum until dry.

Chromatography over neutral silicagel and crystallization from ethanol gave 0.6 g 11$\beta$-acetyl-$\Delta^5$-oestrene-3,17-dione 3,17-diethylene ketal, m.p. 179°–180.5° C.

EXAMPLE XVII

According to a standard procedure for preparingoestradiol 17$\beta$-esters (reacting the 3,17$\beta$-diol with the carboxylic acid chloride in acetone/pyridine and partially hydrolyzing the 3,17$\beta$-diester thus obtained giving the 3,17$\beta$-diol 17$\beta$-ester) 11$\beta$-ethynyl-$\Delta^{1,3,5(10)}$-oestratriene-3,17$\beta$-diol (Example XIV) was converted into the following 17$\beta$-esters thereof:

17$\beta$-undecanoate

17β-cyclo-octylacetate
17β-4',4'-diethyl-hexanoate.

What is claimed is:

1. A compound of the formula:

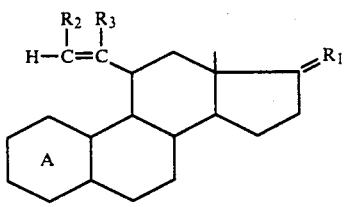

wherein:
(a) R₁ is O or (αY) (βZ), wherein Y is selected from the group consisting of H, unsaturated aliphatic hydrocarbons of two to about four carbon atoms, saturated aliphatic hydrocarbons of about one to about four carbon atoms, and Z is a free, esterified or etherified hydroxy group;
(b) R₂ is H and R₃ is H or CH₃; in the alternative, R₂ and R₃ together with their linking carbon atoms present form an acetylenic moiety of the formula HC≡C—; and
(c) ring A has the structure:

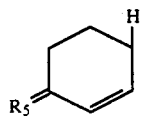

wherein R₅ is O or two hydrogens.

2. The compound as recited in claim 1, wherein R₅ is O, R₁ and R₃ together with their linking carbon atom present form an acetylenic moiety of the formula HC≡C—.

3. The compound as recited in claim 1, wherein R₅ is O, R₁ is (α-ethynyl) (β-OH), and R₂ and R₃ together with their linking carbon atoms present form an acetylenic moiety of the formula HC≡C—.

4. The compound as recited in claim 1, wherein R₅ is O, R₁ (α-ethyl) (β-hydroxy), and R₂ and R₃ together with their linking carbon atoms present form an acetylenic moiety of the formula HC≡C—.

5. The compound as recited in claim 1, wherein R₅ is O, R₁ is O, and R₂ is H and R₃ is CH₃.

6. The compound as recited in claim 1, wherein R₅ is O, R₁ is O, and R₂ and R₃ are each H.

7. The compound as recited in claim 1, wherein R₅ is O, R₁ is (α-ethynyl) (β-OH), and R₂ and R₃ are each H.

8. The compound as recited in claim 1, wherein R₅ is H₂, R₁ is (α-ethynyl) (β-OH), R₂ and R₃ are each H.

9. The compound as recited in claim 1, wherein R₅ is O, R₁ is (α-H) (β-OH), and R₂ and R₃ are each H.

10. The compound as recited in claim 1, wherein R₅ is O, R₁ is (α-H) (β-OH), and R₂ and R₃ together with their linking carbon atoms present form an acetylenic moiety of the formula HC≡C—.

11. The compounds as recited in claim 1, wherein R₅ is O, R₁ is (α-H) (β-decanoate), and R₂ and R₃ are each H.

12. The compounds as recited in claim 1, wherein R₅ is O, R₁ is (α-H) (β-decanoate), and R₂ and R₃ together with their linking carbon atoms present form an acetylenic moiety of the formula HC≡C—.

13. The compound as recited in claim 1, wherein R₅ is O, R₁ is (α-H) (β-cyclo-octylacetate), and R₂ and R₃ with their linking carbon atoms present form an acetylenic moiety of the formula HC≡C—.

14. The compound as recited in claim 1, wherein R₅ is O, R₁ is (α-H) (β-cyclo-octylacetate), and R₂ and R₃ are each H.

15. The compound as recited in claim 1, wherein R₅ is two hydrogens, R₁ is (α-H) (β-OH), and R₂ and R₃ are each H.

16. The compound as recited in claim 1, wherein R₅ is H₂, R₁ is (α-ethynyl) (β-OH) and R₂ and R₃ together with their linking carbon atoms present form an acetylenic moiety of the formula HC≡C—.

17. The compound as recited in claim 1, wherein R₅ is two hydrogens, R₁ is (α-vinyl) (β-OH) and R₂ and R₃ are each H.

18. The compound as recited in claim 1, wherein R₅ is O, R₁ is (α-ethynyl) (β-OH), R₂ is H and R₃ is CH₃.

19. The compound as recited in claim 1, wherein R₅ is H₂, R₁ is (α-H) (β-OH), and R₂ and R₃ together with their linking carbon atoms present form an acetylenic moiety of the formula HC≡C—.

20. The compound as recited in claim 1, wherein R₅ is H₂, R₁ is (α-allyl) (β-OH), and R₂ and R₃ together with their linking carbon atoms present form an acetylenic moiety of the formula HC≡C—.

21. The compoud as recited in claim 1, wherein R₅ is H₂, R₁ is (α-ethynyl) (β-OH), R₂ is H and R₃ is CH₃.

22. The compound

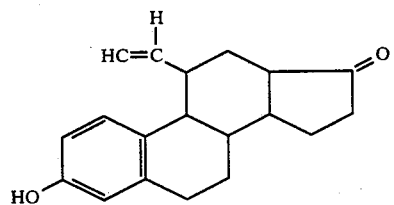

23. A compoound of the formula

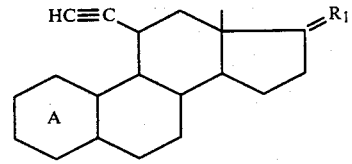

wherein
(a) R₁ is O or (αY) (βZ), wherein Y is selected from the group consisting of H, unsaturated aliphatic hydrocarbons of two to about four carbon atoms, saturated aliphatic hydrocarbons of about one to about four carbon atoms, and Z is a free, esterified or etherified hydroxy group; and
(b) ring A has the structure:

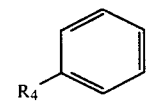

wherein R₄ is a free, esterified or etherified hydroxyl group.

24. The compound as recited in claim 23, wherein R₄ is OH and R₁ is O.

25. The compound as recited as claim 23, wherein $R_4$ is OH and $R_1$ is ($\alpha$-H) ($\beta$-OH).

26. The compound as recited in claim 23, wherein $R_4$ is OH and $R_1$ is ($\alpha$-ethynyl) ($\beta$-OH).

27. The compound as recited in claim 23, wherein $R_4$ is OH and $R_1=(\alpha H)$ ($\beta$-undecanoate).

28. The compound as recited in claim 23, wherein $R_4$ is OH and $R_1=(\alpha H)$ ($\beta$-cyclo-octylacetate).

29. The compound as recited in claim 23, wherein $R_4$ is OH and $R_1=(\alpha H)$ ($\beta$-4',4'-diethylhexanoate).

* * * * *